(12) United States Patent  
Bierman

(10) Patent No.: US 6,689,104 B2
(45) Date of Patent: Feb. 10, 2004

(54) MEDICAL LINE SECUREMENT DEVICE

(75) Inventor: Steven F. Bierman, Del Mar, CA (US)

(73) Assignee: Venetec International, Inc., San Diego, CA (US)

( * ) Notice: Subject to any disclaimer, the term of this patent is extended or adjusted under 35 U.S.C. 154(b) by 0 days.

(21) Appl. No.: 10/213,756

(22) Filed: Aug. 6, 2002

(65) Prior Publication Data

US 2002/0187259 A1 Dec. 12, 2002

Related U.S. Application Data

(60) Continuation of application No. 09/845,630, filed on Apr. 30, 2001, now Pat. No. 6,428,516, which is a division of application No. 08/970,223, filed on Nov. 14, 1997, now Pat. No. 6,224,571.

(51) Int. Cl.[7] ................................................ A61M 5/32
(52) U.S. Cl. ....................................... 604/174; 604/180
(58) Field of Search ................................ 604/174, 177, 604/179, 180, 523; 128/DIG. 26

(56) References Cited

U.S. PATENT DOCUMENTS

| 2,525,398 | A | 10/1950 | Collins |
| 2,707,953 | A | 5/1955 | Ryan |
| 3,059,645 | A | 10/1962 | Hasbrouck et al. |
| 3,064,648 | A | 11/1962 | Bujan |
| 3,482,569 | A | 12/1969 | Raffaelli, Sr. |
| 3,613,663 | A | 10/1971 | Johnson |
| 3,630,195 | A | 12/1971 | Santomieri |
| 3,677,250 | A | 7/1972 | Thomas |
| 3,766,915 | A | 10/1973 | Rychlik |
| 3,834,380 | A | 9/1974 | Boyd |
| 3,856,020 | A | 12/1974 | Kovac |
| 3,906,946 | A | 9/1975 | Nordströöm |
| 3,973,565 | A | 8/1976 | Steer |
| 4,020,835 | A | 5/1977 | Nordstrom et al. |
| 4,057,066 | A | 11/1977 | Taylor |
| 4,059,105 | A | 11/1977 | Cutruzzula et al. |
| 4,129,128 | A | 12/1978 | McFarlane |
| 4,161,177 | A | 7/1979 | Fuchs |
| 4,224,937 | A | 9/1980 | Gordon |
| 4,248,229 | A | 2/1981 | Miller |
| 4,250,880 | A | 2/1981 | Gordon |

(List continued on next page.)

FOREIGN PATENT DOCUMENTS

| EP | 0064284 A2 | 10/1982 | |
| EP | 356.683 A | 3/1990 | |
| FR | 2381529 | 9/1978 | |
| GB | 2211417 | 7/1989 | ................. 604/180 |
| WO | WO 92/19309 | 11/1992 | |

*Primary Examiner*—Sharon Kennedy
(74) *Attorney, Agent, or Firm*—Knobbe Martens Olson & Bear LLP

(57) ABSTRACT

A securement device includes a simply-structured retention mechanism that permits a portion of a catheter hub or a similar medical article to be easily anchored to a patient, without the use of tape or needles and suturing. A unitary retainer desirably includes a base defining a locator mechanism. The locator mechanism interacts with a fitting of the medical device so as to position the medical device relative to the retainer. The locator mechanism also desirably guides the medical device fitting into contact with an adhesive member mounted on an outer surface of the retainer. In one form, the locator mechanism includes one or more posts that engage mating holes defined in the medical device fitting. In other forms, the locator mechanism includes a cradle defining an arcuate channel to receive a convex surface of the medical device, or a recess shaped to matingly receive the fitting. The retainer is attached to a flexible anchor pad that includes an adhesive bottom surface, which can be attached to the patient's skin. In use, a health care provider positions the medical device fitting on the retainer in a position established and guided by the locator mechanism, and attaches the fitting to the retainer via the adhesive member.

18 Claims, 7 Drawing Sheets

U.S. PATENT DOCUMENTS

| | | |
|---|---|---|
| 4,316,461 A | 2/1982 | Marais et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,449,975 A | 5/1984 | Perry |
| 4,453,933 A | 6/1984 | Speaker |
| 4,480,639 A | 11/1984 | Peterson et al. |
| 4,711,636 A | 12/1987 | Bierman |
| 4,742,824 A | 5/1988 | Payton et al. |
| 4,808,162 A | 2/1989 | Oliver |
| 4,822,342 A | 4/1989 | Brawner |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,955,864 A | 9/1990 | Hajduch |
| 4,976,700 A | 12/1990 | Tollini |
| 5,037,397 A | 8/1991 | Kalt et al. |
| 5,073,170 A | 12/1991 | Schneider |
| 5,084,026 A | 1/1992 | Shapiro |
| 5,098,399 A | 3/1992 | Tollini |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,236,421 A | 8/1993 | Becher |
| 5,266,401 A | 11/1993 | Tollini |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman et al. |
| 5,338,308 A | 8/1994 | Wilk |
| 5,342,317 A | 8/1994 | Claywell |
| 5,344,406 A | 9/1994 | Spooner |
| 5,354,282 A | 10/1994 | Bierman |
| 5,372,589 A | 12/1994 | Davis |
| 5,380,293 A | 1/1995 | Grant |
| 5,380,395 A | 1/1995 | Uchida |
| 5,403,285 A | 4/1995 | Roberts |
| 5,413,562 A | 5/1995 | Swauger |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,147,322 A | 1/1996 | Bowen et al. |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,527,293 A | 6/1996 | Zamierowski |
| D375,355 S | 11/1996 | Bierman |
| 5,578,013 A | 11/1996 | Bierman |
| 5,593,395 A | 1/1997 | Martz |
| 5,685,859 A | 11/1997 | Kornerup |
| 5,693,032 A | 12/1997 | Bierman |
| 5,722,959 A | 3/1998 | Bierman |
| 5,810,781 A | 9/1998 | Bierman |
| 6,132,399 A | 10/2000 | Shultz |
| 6,213,979 B1 | 4/2001 | Bierman |

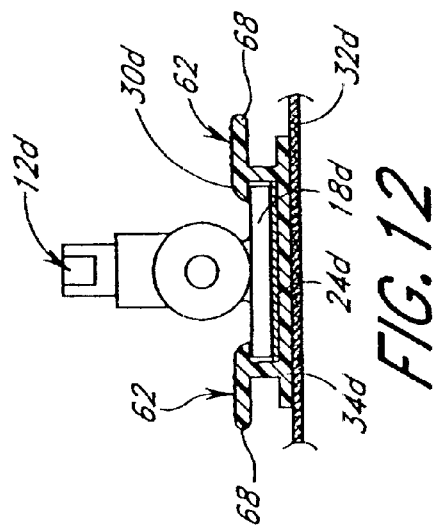
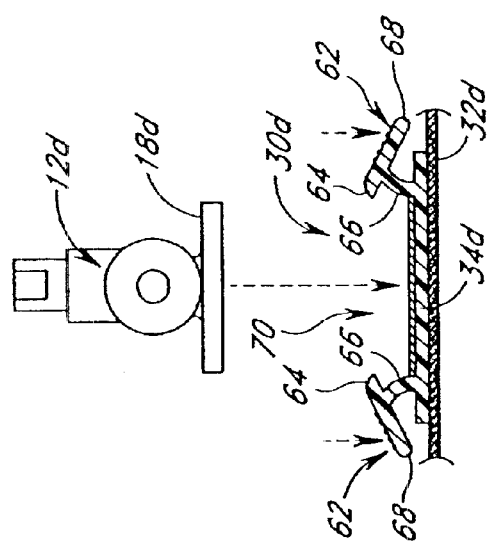
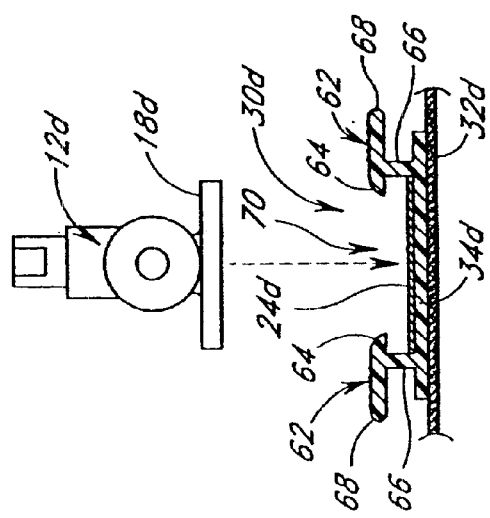

MEDICAL LINE SECUREMENT DEVICE

RELATED APPLICATION

This application is a continuation application of application Ser. No. 09/845,630, filed on Apr. 30, 2001, which issued on Aug. 6, 2002 as U.S. Pat. No. 6,428,516 and which is a divisional application of application Ser. No. 08/970,223, filed on Nov. 14, 1997, which issued on May 1, 2001 as U.S. Pat. No. 6,224,571.

BACKGROUND OF THE INVENTION

1. Field of the Invention

The present invention relates to a securement device for securing a medical line or article to a patient.

2. Description of Related Art

Medical treatment of patients commonly involves the use of percutaneously inserted catheters to direct fluids directly into the bloodstream, a specific organ or an internal location within the patient, or to monitor vital functions of the patient. For instance, short, peripherally-inserted, intra-arteriovenous catheters are commonly used to direct fluids and/or medications directly into the bloodstream of the patient.

The fluid (e.g., parenteral liquid, medication, etc.) typically drains from a container positioned above the patient to feed under gravity or is delivered via an infusion pump. The fluid flows through tubing and thence into the indwelling catheter. The catheter and the fluid tubing are commonly removably attached to each other by a conventional luer-lock connector.

In common practice, a health care provider uses adhesive, foam or surgical tape to maintain the catheter in place on the skin of the patient. The health care provider wraps a thin piece of tape around the hub of the catheter and then forms a "chevron" with the tape, placing the ends next to the sides of the indwelling catheter. The health care provider then places one piece of across and over the catheter hub, forms a loop in the tubing, places another piece of tape across the tubing loop, and places yet an additional piece of tape over the catheter hub and the tubing section that has been looped around and extends next to the indwelling catheter. Subsequently, the health care provider typically covers the insertion site and the indwelling catheter with a transparent dressing.

The entire taping and dressing procedure takes several minutes of the health care provider's valuable time. In addition, the catheterization process often requires relatively frequent disconnection between the catheter and the fluid supply tube, as well as dressing changes. For instance, intravenous catheterization is frequently maintained for several days, depending upon the condition of the patient. The tubing is generally replaced every 48 to 72 hours in order to maintain the sterility of the fluid and the free-flow of the fluid through the tubing. A health care provider thus must frequently change the tubing and re-tape the connection. The health care provider also must frequently clean the insertion site about the indwelling catheter and change the dressings.

The health care provider thus uses a great deal of valuable time applying, removing and reapplying tape. The frequent application and removal of the tape also commonly excoriates the patient's skin about the insertion site.

In addition, the traditional method of intravenous catheter securement—surgical tape and transparent dressings alone—have not always prevented catheter migration and/or dislodgment. Taped intravenous catheters are also easily pulled out during a "routine" dressing change, especially by inexperienced health care providers. And if the catheter migrates too far or dislodgment occurs, the health care provider must replace the catheter, thus exacerbating the time and expense required to maintain the intravenous feed.

Prior securement methods also have not served the patient well. Surgical tape or foam strips are uncomfortable. Many patients also do not rest comfortably and worry about catheter dislodgment when they move, when only tape and a dressing secure the catheter in place.

Several additional drawbacks result from the use of tape to stabilize the catheter. One is contamination. Health care providers often tear off small strips of tape and place then on the hand rail on the patient's bed. Clostridium and other bacteria, however, commonly exist on these surfaces and can be transferred to the patient's skin in the proximity of the insertion site.

In addition, tape securement requires the nurse to handle the tape while wearing protective latex gloves. Tearing adhesive tape tends to produce microscopic and/or visible holes in the gloves and thus destroys glove barrier protection.

A number of catheterization systems have been developed to improved the stability of the catheter and to obviate the need for frequent application and removal of surgical tape. Prior devices, however, have generally held the connector on the IV tubing securely against the patient, rather than the catheter fitting itself.

SUMMARY OF THE INVENTION

The present invention involves the recognition that where (i) the catheter securement device secures the connector on the tubing, rather than the catheter fitting, and (ii) the interconnection between the tube connector and the catheter fitting occurs across a bendable anatomic joint (e.g., the patient's wrist), a possibility exists for relative movement to occur between the indwelling catheter and the corresponding vessel (e.g., vein). As a result of such movement, the catheter under some circumstances may become dislodged, requiring re-catheterization of the IV catheter, re-securement of the catheter, and redressing of the insertion site. Again, such catheter migration and/or dislodgment leads to increased time and expense associated with maintaining an intravenous feed.

A need therefore exists for a simply-structured securement device that retains a medical line in a fixed position on a patient's body, but releases the medical line for dressing changes or other maintenance, even where the catheter-tubing connection spans an anatomic joint. An additional need exists for a securement device that incorporates a versatile medical line retaining mechanism, i.e. a device that can be used to attach one of a variety of medical line fittings to an insertion site on a patient's body.

One aspect of the present invention involves a securement device system for securing a medical line to a body of a patient. The securement device comprises a mounting surface that is at least partially covered by an adhesive layer for attaching the securement device to the patient's body. A receiving surface is located distal of the mounting surface. An adhesive member at least partially covers the receiving surface and is positioned to contact at least a portion of the medical line secured by the securement device. A locator mechanism interacts with the medical line and positions the medical line portion on the receiving surface relative to the adhesive member.

A preferred method of manufacturing a medical line securement device involves affixing a sheet of a backing material to a sheet of adhesive-backed foam material, then cutting a first pattern through the sheet of foam material without cutting through the sheet of backing material, the first pattern at least partially defining an anchor pad. A second pattern is then cut through both the sheet of foam material and the sheet of backing material, the second pattern defining on the backing material a release layer for exposing the adhesive backing of the anchor pad prior to attaching the securement device to the patient's body. A retainer is formed (e.g., molded, or extracted) to include a locator mechanism that is adapted to interact with a portion of the medical line and to thereby guide the medical line into a position relative to the retainer. The retainer is attached to a surface of the anchor pad, and a patch of an adhesive material is applied to a surface of the retainer. A release layer is affixed over the adhesive patch, but is removable to expose the adhesive patch during use.

A preferred method of securing a medical line to a patient involves providing a securement device having a first adhesive member on one side, a second adhesive member on an opposite side, and a locator mechanism. The locator mechanism is engaged with a portion of the medical device so as to position the medical device portion generally over the first adhesive member. The medical device thence is engaged with the first adhesive member to secure the medical device to the securement device. The second adhesive member is placed on the patient's body to secure the securement device, and thus the retained portion of the medical line, to the patient.

Further aspects, features, and advantages of the present invention will become apparent from the detailed descriptions of the preferred embodiments that follow.

BRIEF DESCRIPTION OF THE DRAWINGS

The illustrated embodiments of the securement device are intended to illustrate, and not to limit the invention, and contain the following figures:

FIG. 10 is a cross-sectional view of the securement device of FIG. 9, taken along the line 10—10;

FIG. 11 is a cross-sectional view of the securement device according to FIG. 10, but with tangs shown in an open position;

FIG. 12 is a cross-sectional view of the securement according to FIG. 10, but with a fitting of the medical line in the latched position;

DETAILED DESCRIPTION OF PREFERRED EMBODIMENTS OF THE INVENTION

The present embodiments of the medical line securement device are disclosed in the context of an exemplary intravenous (IV) catheter. The principles of the present invention, however, are not limited to IV catheters. Instead, it will be understood by one of skill in this art, in view of the present disclosure, that the securement devices and retainers disclosed herein also can be successfully utilized in connection with other types of medical lines, including tubes for fluid communication and electrical wires. For example, but without limitation, the retainers disclosed herein can be adapted to retain CVCs, PICCs, Foley catheters, and hemodialysis catheters, surgical drainage tubes, feeding tubes, chest tubes, nasogastric tubes, scopes, as well as with electrical wires or cables connected to external or implanted electronic devices or sensors. One skilled in the art may also find additional applications for the devices and devices disclosed herein. Thus, the illustrations and descriptions of securement devices disclosed herein in connection with a catheter are merely exemplary of one possible application of the device.

Each of the embodiments described herein employ the same basic concepts characteristic of the improved securement device, namely attachment of a medical line or article to a patient by use of an adhesive member that adheres to the medical line or article. The securement devices also all include interacting structure that operates between the securement devices and a portion of the medical line or article (e.g., a fitting which either is releasably attached to the medical line or article or is integrally formed with the medical line or article). The interacting structure between the retainer and the portion of the medical line or article generally inhibits relative movement between the medical line and the securement devices in at least one degree of freedom. This interaction also properly locates the portion of the medical line or article on the securement device and guides the medical line or article portion into contact with the adhesive member.

Figure 1:
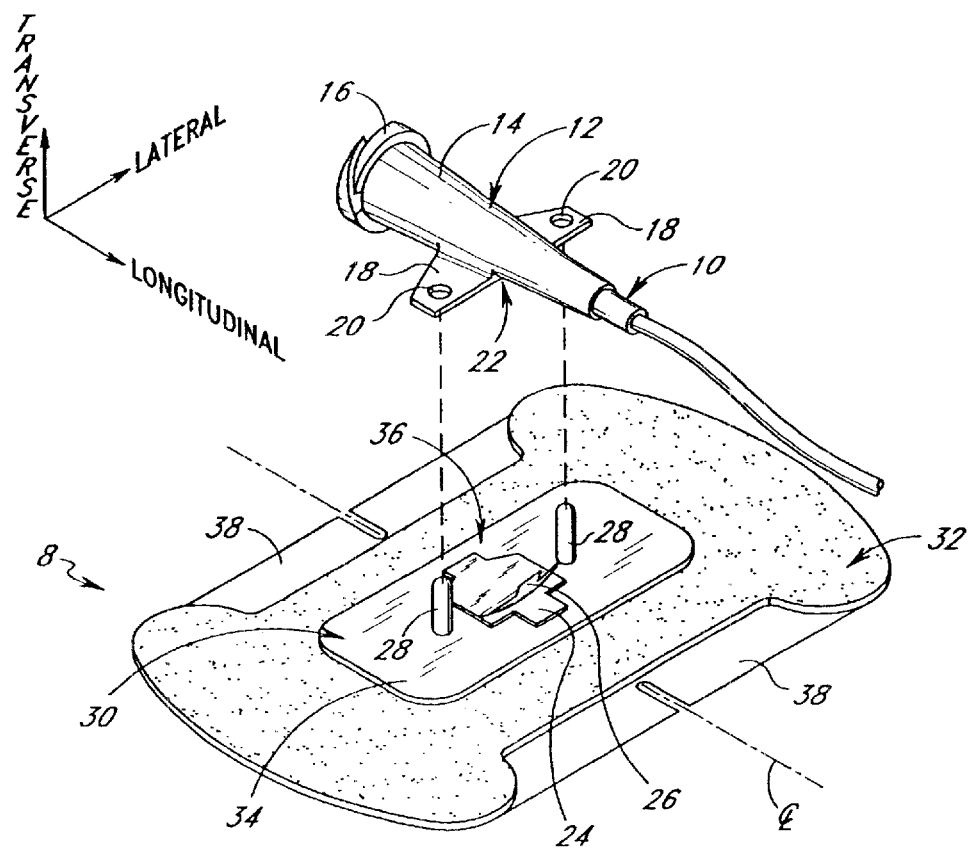
FIG. 1 is a perspective view of a medical line securement device configured in accordance with a preferred embodiment of the present invention, and illustrates an exemplary catheter hub positioned above the securement device.

To assist in the description of the components of the securement devices and retainers disclosed herein, the following coordinate terms are used. A longitudinal axis is generally parallel to a section of the medical line to be retained by the securement device, generally in the plane of a base or pad of the securement device (discussed below). A lateral axis is generally perpendicular to the longitudinal axis within the plane of the base. A transverse axis extends transverse to both the longitudinal and lateral axes. FIG. 1 illustrates this coordinate system to the side of the securement device. The illustrated coordinate system applies to the perspective views of each of the preferred embodiments illustrated herein. In addition, as used herein, the "longitudinal direction" refers to a direction substantially parallel to the longitudinal axis. "The lateral direction" refers to a direction substantially parallel to the lateral axis. And, "the transverse direction" refer to a direction substantially parallel to the transverse axis. These coordinates are used to describe structures and movement of the securement device of each embodiment. A detailed description of each embodiment, and its associated method of use, now follows.

Figure 2:
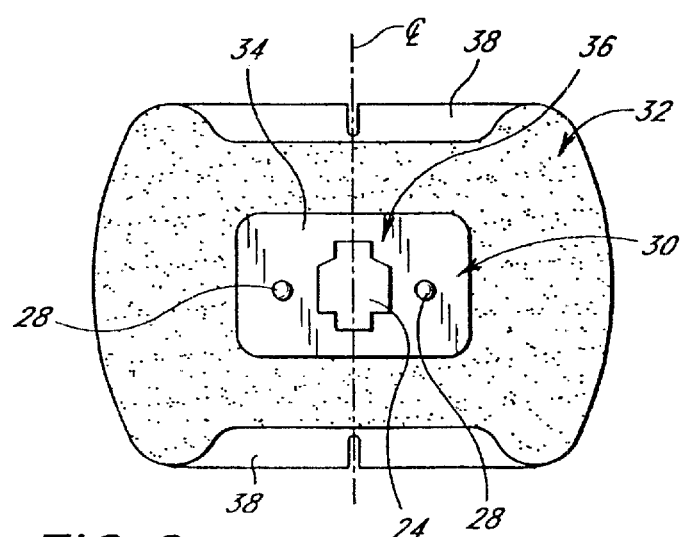
FIG. 2 is a top plan view of the securement device of FIG. 1.

FIGS. 1–2 illustrate an securement device 8 constructed in accordance with a preferred embodiment of the present invention. The securement device 8 is configured to retain a catheter 10, either directly or by way of a fitting 12, as in the illustrated embodiment. Thus, the following description first provides a brief description of the catheter fitting 12 before describing the securement device 8 in order to aid the reader's understanding of this embodiment.

FIG. 1 illustrates an exemplary short, peripheral IV catheter, such as the type available from B. Braun Mesungen AG. The fitting 12 of this catheter 10 includes a conical receptacle 14 in fluid communication with the catheter 10 and having a threaded rim 16 for releasably attaching to a fluid tubing (not shown) to place the tubing in fluid communication with the catheter 10. The fitting 12 also includes a pair of lateral wings 18 that extend roughly perpendicularly from a lower portion of the fitting 12. Each wing 18 includes a through-hole 20. A medial surface 22 of the fitting 12, including portions of the lateral wings 18, has a generally flat, cruciform-shaped foot print.

The securement device 8 receives and directly anchors the catheter fitting 12 to the patient, rather than holding a point in the medical line upstream of the catheter 10 (e.g., the connector between the catheter and the fluid supply tube). For this purpose, the securement device 8 includes an adhesive member 24 against which the medial surface 22 of the catheter fitting 12 is placed. Desirably, the shape of the adhesive member 24 generally corresponds to the shape of catheter fitting's foot print, and the adhesive member 24 is coextensive with or slightly smaller than the size of the fitting's foot print. Thus, in the illustrated embodiment, the adhesive member 24 has generally a cruciform shape.

The adhesive member 24 desirably has a sufficient thickness and tackiness to either secure and/or encapsulate (at least to some degree) the catheter fitting 12 in order to inhibit relative movement between the securement device 8 and the catheter fitting 12. The adhesive member 24 can be applied to the securement device 8 in any of a variety of conventional ways, such as by transfer technology (e.g., thin film transfer tape) or by sputtering. For instance, in the illustrated embodiment, the adhesive member 24 is formed of a transfer adhesive available from Minnesota Mining and Manufacturing Company (3M), of Minneapolis, Minn., as Part No. 950.

As seen in FIG. 1, a release layer 26 can initially cover the adhesive layer 24 before use. In the alternative, the packaging (not shown) for the securement device 8 can function as the release layer 24. In either case, a suitable material covers the adhesive member 24 prior to the securement device's application on a patient. Such suitable material includes, for example, but without limitation, a polycoated, siliconized paper.

The securement device 8 also includes a locator mechanism to properly position the catheter fitting 12 on the adhesive member 24. Any of a wide variety of locator mechanism can be used for this purpose, as illustrated by the various embodiments described below. For instance, as seen in FIGS. 1 and 2, the securement device 8 desirably includes at least one post 28 which cooperates with one of the holes 20 in the catheter fitting wings 20.

In the illustrated embodiment, the securement device 8 desirably includes a pair of posts 28; however, the securement device 8 can also include additional posts to suit a specific application. For example, where the securement device is designed to secure a relatively large fitting, the securement device can include four posts arranged at the corners of a rectangle, for greater stability. As another example, three posts can be used to firmly anchor a Y-site fitting.

The posts 28 can have any of a variety of lengths and diameters, as well have a variety of distances between them, depending upon the particular application and the particular catheter fitting with which they are to interact. For applications with known catheters, each post 28 desirably has a length of about 4 mm to 20 mm, and more particularly a length of about 6 mm; however, longer or shorter lengths also are possible. The post diameter desirably is slightly smaller than the corresponding hole 20 of the catheter fitting 12 but is sufficiently large to inhibit significant bending of the post 28 under normal forces experienced on the medical line. The posts 28 desirably are of comprise a polymer plastic material, with a diameter between 0.5 mm and 3 mm, and more preferably with a diameter about 1.7 mm.

The posts 28 are laterally spaced at least wide enough to accommodate the medical line or article to be anchored, and, in the illustrated embodiment, desirably correspond to the spacing between the holes 20 in the catheter fitting wings 18. For application with most known catheters, the posts 28 are spaced apart by a distance between about 5 mm and about 40 mm, and more particularly by a distance equal to about 15 mm.

In the illustrated embodiment, as seen in FIGS. 1 and 2, the securement device 8 includes a retainer, generally designated by reference numeral 30, mounted on a flexible anchor pad 32. The retainer 30 includes a base 34 which supports the locator mechanism (e.g., the posts 28) and the adhesive member 24 of the retainer 30. The base 34 desirably has a planar shape that defined in part a receiving surface (generally designed by reference numeral 36) for the catheter fitting 12. The posts 28 extend generally normal to the receiving surface 36 of the base 34 with the adhesive member 24 located on the receiving surface 36 and between the posts 28.

The base 34 and the posts 28 of the retainer 30 desirably are integrally formed as a unitary piece. This can be accomplished in any of a variety of ways well known to one of skill in the art. For instance, the entire retainer 30 can be injection molded, in order to reduce fabrication costs. Suitable plastics from which the posts 28 and base 34 can be made include, for example, but without limitation, polypropylene, polyethylene, and the like. In particular, acceptable materials include Tenite® 811 low density polyethylene (LDPE) available commercially from Eastman Chemical Company, of Kingsport, Tenn., and polypropylene (#P6M5B-015) and polypropylene copolymer (#P6M5Z-036), both available commercially from Huntsman Chemical, Salt Lake City, Utah.

As mentioned above, the adhesive member 24 can be applied to the base 34 in a variety of ways, including, but without limitation, by transfer tape or sputtering. If applied by transfer tape, the application can be done as part of a converter process, described below.

The base 34 of the retainer 30 is attached to the anchor pad 32. The base 34 desirably is secured to the anchor pad 32 by a solvent bond adhesive, such as cyanoacrylate or other bonding material. One such adhesive is available commercially as Part No. 4693 from 3M.

The anchor pad 32 comprises a flexible structural layer for securing the retainer 30 to a patient's skin. The pad 32 desirably comprises a laminate structure with an upper foam layer (e.g., closed-cell polyethylene foam), and a bottom adhesive layer. The adhesive preferably is a medical-grade adhesive and can be either diaphoretic or nondiaphoretic, depending upon the particular application. The anchor pad 32 desirably is formed from a polyethylene foam tape (1/32 to 1/8 inch thick) with an acrylic adhesive, 40 to 120 grams/square meter thick. Such foam with an adhesive layer is available commercially from New Dimensions in Medicine of Columbus, Ohio.

An upper surface of the foam layer of the anchor pad 32 is roughened by corona-treating the foam with a low electric charge. The roughened or porous upper surface of the anchor pad 32 improves the quality of the adhesive joint formed by the cyanoacrylate (or by another type of adhesive or bonding material) between the base 34 and the anchor pad 32. In the alternative, the flexible anchor pad 32 can comprise a medical-grade adhesive bottom layer, an inner foam layer and an upper paper or other woven or non-woven cloth layer.

A removable paper or plastic backing or liner 38 desirably covers the bottom adhesive surface before use. This release layer 38 preferably resists tearing and is divided into a plurality of pieces to ease attachment of the pad to a patient's skin. In the illustrated embodiment, the backing is a polycoated, siliconized paper.

The backing desirably is split along a center line CL of the flexible anchor pad 32 in order to expose only half of the adhesive bottom surface at one time. The backing 38 also advantageously extends beyond at least one edge of the anchor pad 32, as illustrated, to facilitate removal of the backing 38 from the adhesive layer.

Although not illustrated, the retainer 30 and/or the anchor pad 32 can include suture holes in addition to the adhesive layer to further secure the anchor pad to the patient's skin.

In the illustrated embodiment, the anchor pad 32 also desirably includes a pair of opposing concave sections that narrows the center of the anchor pad 32 proximate to the retainer base 34. As a result, the peripheral ends of the anchor pad 32 have more contact area to provide greater stability and adhesion to a patient's skin, while allowing the retainer 30, which is located at center section of the anchor pad 32, to be placed adjacent to a catheter insertion site.

The anchor pad 32 and release layer 38 (i.e., backing) are formed using a converter process. A sheet of backing material is initially applied onto the adhesive surface of the foam material. (The foam is purchased with a backing; however, a new backing desirably is applied which includes printed indicia that identifies the manufacturer of the securement device 8.)

A first pattern is cut multiple times in the sheet of adhesive-backed foam material through the conversion process. This may be done using a die-cut technique which "kiss-cuts" only the foam material in the first patters without cutting the backing material. The cut first pattern desirably corresponds to at least a portion of the anchor pad 32. That is, the first pattern, which is cut into the foam material, at least partially defines the shape of the anchor pad 32.

A second pattern is then cut multiple times into the sheet of adhesive-backed material (i.e., the foam material) and the backing material. The second pattern defines the balance of the anchor pad shape, as well as the exposed portion of the release layer 38. This process likewise can be done by die-cutting.

The release liner 38 also is cut into its two halves without cutting the foam layer. This process can be done either before or after the second pattern is cut and also can be accomplished by a die cut. Multiple anchor pads thus are produced from a single sheet the foam/adhesive/backing laminate structure through this conversion process.

In use, the health care provider removes the securement device from its protective, sterile packaging (not shown) and peals off the release layer 26 from the adhesive member 24 if provided separate from the packaging. Otherwise, the adhesive member 24 emerges uncovered from the packaging. The health care provider then aligns the posts 28 with suture holes 20 in the catheter fitting wings 18 and inserts the posts 28 into the holes 20. The interaction between the holes 20 and the posts 28 properly positions the catheter fitting 12 on the retainer 30. The health care provider then moves the catheter fitting 12 into contact with the adhesive member 24 and presses the catheter fitting 12 against the retainer 30 to ensure good contact between the adhesive member 24 and the medial surface 22 of the catheter fitting 12. As a result of the corresponding shapes of the adhesive member 24 and medial surface 22 of the catheter fitting 12, the medial surface 22 completely covers the adhesive member 24, thereby inhibiting exposure of the adhesive member 24. Because exposed adhesive can become sites for bacterial growth, minimizing such exposure substantially reduces the risk of a insertion site infection.

The health care provider desirably secures the anchor pad 32 to the patient after attaching the catheter fitting 12 to the retainer 30. This step can be done before catheter fitting attachment, but it requires placing the anchor pad 32 on the patient in a position precisely aligning the retainer 30 beneath the catheter fitting 12. Regardless of the order of these acts, the health care provider secures the anchor pad to the patient by first removing one half of the release layer and pressing the anchor pad against the patient's skin, adhesive side face down. The health care provider then removes the other half of the release layer and smoothes the anchor pad 32 against the patient. The securement device 8 in this position securely anchors the catheter fitting 12 to the patient.

Figure 3:
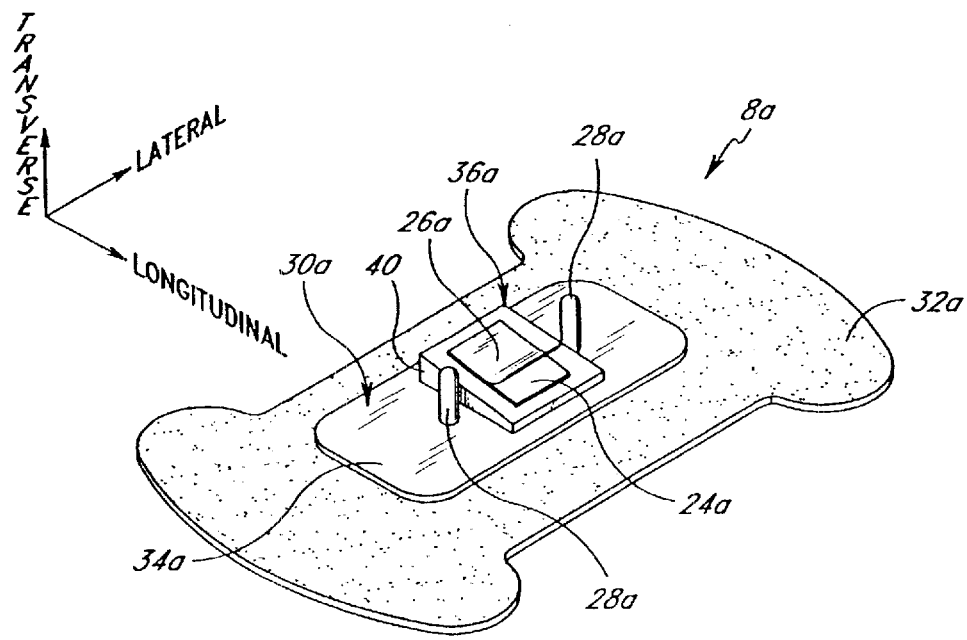
FIG. 3 is a perspective view of a securement device configured in accordance with another preferred embodiment of the present invention.

FIG. 3 illustrates a medical line securement device 8a in accordance with another embodiment of the present invention. The above description in relation to FIGS. 1 and 2 applies equally to the embodiment of FIG. 3, unless otherwise indicated. In addition, like reference numerals are used to indicate like features among the embodiments, with the letter "a" added as a suffix to refer to features of the present embodiment.

The securement device 8a comprises a retainer 30a. The retainer 30a is similar to the retainer illustrated in FIGS. 1–2, except that the base 34a of the retainer 30a comprises a raised pedestal 40 extending upwardly from the base 34a and defining a portion of the receiving surface 36a. The raised pedestal 40, the base 34a and the posts 28a desirably are all integrally formed in an unitary retainer 30a.

The adhesive member 24a is formed on an upper surface of the raised pedestal 40, and a release layer 26a covers the adhesive member 24a. Alternatively, the packaging (not shown) functions as the release layer, as described above.

The raised pedestal 40 of the retainer 30a preferably has a planar upper surface on which the adhesive layer 24a is located. Desirably, the plane generally defined by the upper surface of the raised pedestal 40 desirably forms an acute angle with the planar surface of the base 34a. The angled upper surface imparts an angular orientation to the catheter fitting relative to the patient's skin. The resulting incident angle desirably ranges between about 0° and 15°, depending upon the application of the catheter securement device 8, as known in the art.

An anchor pad 32a supports the retainer 30a. A release layer (not shown) covers an adhesive underside of the anchor pad 32a prior to application of the anchor pad 32a to the patient, as described above.

Figure 4:
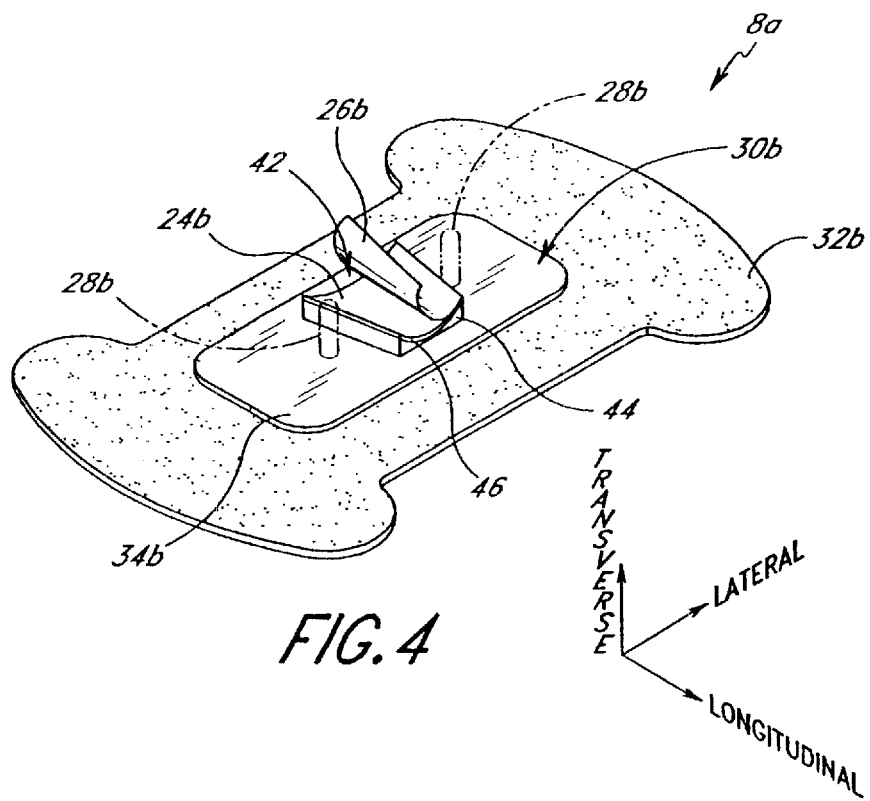
FIG. 4 is a perspective view of a securement device configured in accordance with an additional preferred embodiment of the present invention.
Figure 5:
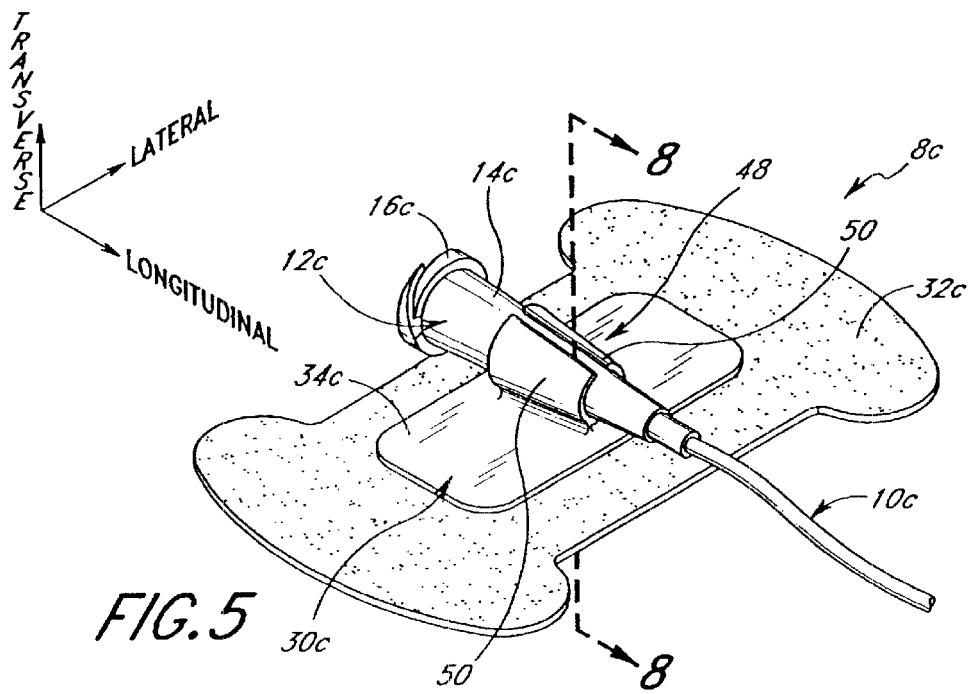
FIG. 5 is a perspective view of a securement device configured in accordance with another preferred embodiment of the present invention, and illustrates an exemplary catheter hub in a retained position.

FIG. 4 illustrates a medical line securement device 8b in accordance with another embodiment of the present invention. The above description with respect to the embodiment of FIGS. 1 and 2 applies equally to the embodiment of FIG. 4, unless otherwise indicated. In addition, like reference numerals are used to indicate like features among the embodiments, with the letter "b" added as a suffix to refer to features of the present embodiment of FIG. 4.

The retainer 30b is similar to the retainer of FIG. 1, except that the retainer 30b includes a cradle 42 extending upwardly from the base 34b of the retainer 30b. The adhesive member 24b desirably lies within the cradle 42 and covers at least a portion of the receiving surface 38b defined by the cradle 42. A release layer 26b can initially cover the adhesive member 24b, or the packaging can serve this function, as described above.

In addition, a foam layer 46 desirably is interposed between the surface of the channel 44 and the adhesive layer 24b. The foam layer 46 provides for good contact between the adhesive layer 24b and the surface of the catheter fitting, despite the presence of protuberances on the surface of the catheter fitting. That is, the foam layer 46 allows the adhesive layer 24b to follow the contours of the juxtaposed catheter fitting surface.

The cradle 42 preferably has a concave, arcuate upper surface that forms a channel 44 and functions as the receiving surface of the retainer 30b. Desirably, the surface of the channel 44 conforms substantially to a portion of a surface of a cone, thereby allowing the channel to mate easily with a conically-shaped catheter fitting, such as the fitting illustrated in FIG. 1. Because the arcuate surface of the channel 44 can be used to guide a catheter fitting into a desired position relative to the retainer 30b and onto the adhesive layer 24b, posts 28b (shown in phantom lines in FIG. 4) are optional in the present embodiment. Such posts 28b, in conjunction with corresponding suture holes, such as the holes 20 in the catheter fitting wings (see FIG. 1), may make it easier for a health care provider to position a catheter fitting relative to the retainer 10c and therefore may be used if desired. In this embodiment, both the shape of the channel 44 and the posts 28b, if included, function as the locator mechanism of the retainer 30b.

An anchor pad 32b supports the retainer 30b. A release layer (not shown) desirably covers an adhesive underside of the anchor pad 32b prior to application of the anchor pad 32b to the patient, as described above.

FIGS. 5–8 illustrate a medical line securement device 8c in accordance with another embodiment of the present invention. The above description with respect to the embodiment of FIGS. 1 and 2 applies equally to the embodiment of FIGS. 5–8, unless otherwise indicated. Like reference numerals are used to indicate like features among the embodiments, with the suffix "c" added to refer to features of the present embodiment.

The retainer 30c and anchor pad 32c of securement device 8c are similar to those illustrated in FIG. 1, except that the locator mechanism takes the form of a cradle 48 with movable walls 50. The adhesive member 24c desirably lies within the cradle 48 and covers at least a portion of the receiving surface as defined by the cradle 48. A release layer (not shown) can initially cover the adhesive member 24c or the packaging can serve this function, as described above.

Figure 6:
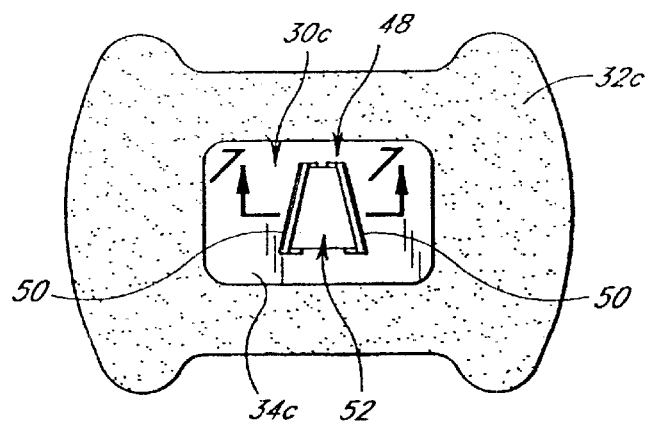
FIG. 6 is a top plan view of the securement device of FIG. 5 in an open position without the retained catheter hub.
Figures 7, 8:
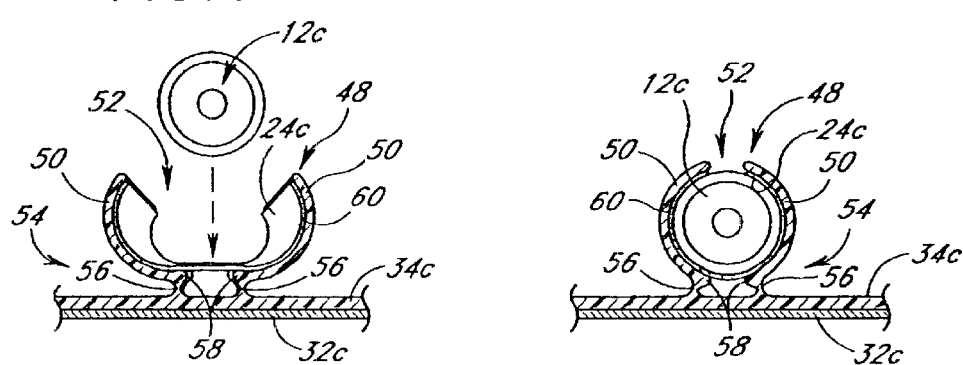
FIG. 7 is a cross-sectional view of a portion of the securement device of FIG. 6 taken along line 7—7, and illustrates with the securement device in an open position with the catheter hub positioned above the securement device.
FIG. 8 is a cross-sectional view of securement device of FIG. 5 taken along line 8—8 and illustrates the securement device in a closed position receiving the catheter hub.
Figure 9:
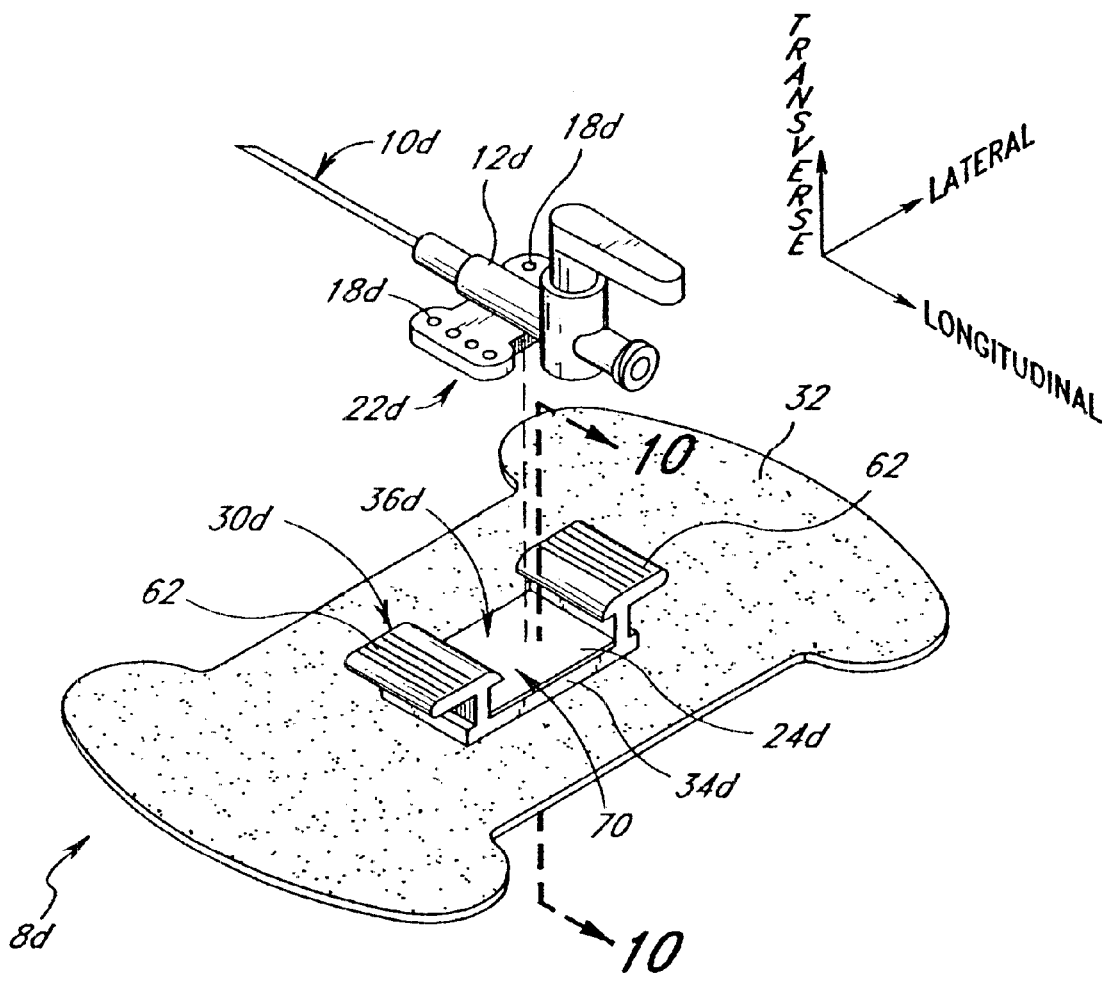
FIG. 9 is a perspective view of a medical line securement device configured in accordance with an additional preferred embodiment of the present invention and illustrates a catheter fitting positioned above the securement device.

As best understood from FIGS. 6, 7 and 8, the cradle includes a channel 52 of tapering width, which includes an arcuate surface that functions as the receiving surface of the retainer 30c. Desirably, the shape of the channel 52 conforms substantially to a portion of a cone (i.e., has a frusto-conical shape), thereby allowing the channel 52 to mate easily with a conically-shaped section of the catheter fitting 12c.

The channel 52 is defined in part by the opposing wall sections 50. Each wall section 50 has an arcuate shape of a radius of curvature that generally matches the catheter fitting 12c. Each wall section 50 also extends through an arc length of generally greater than 90□ such that together the wall sections 50 surround at least 180□ of the conical-shaped catheter fitting 12c.

A flexible coupling, generally identified by reference numeral 54, interconnects the wall sections 50 of the cradle 48 and supports the cradle 48 about retainer base 34c. In the illustrated embodiment, the flexible coupling 54 is integrally formed with the base 34c, as well as with the wall sections 50. The flexible coupling 54 includes a pair of generally parallel rails 56. Each rail 56 includes a necked-down section formed between the base 34c and the corresponding wall section 50. This neck section is flexible and permits the corresponding wall section 50 to move relative to the base 34c.

The wall sections 50 thus are movable relative to each other and to the base 34c. Desirably, the flexible coupling 54 normally holds the wall sections 50 in an open position, as illustrated in FIG. 7, in which the upper ends (distal of the base 34c) of the wall sections 50 are spaced apart. The flexible coupling 54 permits the wall sections 50 to move toward each other into a closed position, as seen in FIG. 8. In this position, the upper ends of the wall sections 50 are spaced closely together, and the channel's shape and size generally matches that of the retained section of the catheter fitting 12c. The cradle 48 in the closed position thus extends more than 180□ around the circumference of the catheter fitting 12c.

The flexible coupling 54 also includes an actuator mechanism to move the wall sections into the closed position once the channel 52 has received the catheter fitting 12c. In the illustrated embodiment, the actuator mechanism includes a pair of lugs 58 that extend from the lower ends of the wall sections 50 between the rails 56. Each lug 58 has an inner surface (i.e., a surface within the channel 52) with an arcuate shape that generally matches that of the corresponding wall section 50. The lugs 50 are also oriented and sized to have a slight upwardly orientation when the cradle 48 is in the open position,, as seen in FIG. 7. But when the catheter fitting 12c is pressed into the channel 52, the lugs 58 move downward. The downward movement of the lugs 58 causes the attached wall section 50 to pivot about the corresponding rail 56 with the neck section of the rail 56 flexing, as seen in FIG. 8.

A foam layer 60 is placed within the channel 52 and lines at least a portion of the channel's surface. The foam layer 60 not only compensates for irregularities in the catheter fittings surface, but it also acts as a substrate for the adhesive member 24c. In the illustrated embodiment, the foam layer 60 and the adhesive layer 24c line the entire inner surface of the cradle's channel 52.

In use, the conical section of the catheter fitting 12c is inserted into the cradle 48 while the flexible coupling 54 holds the cradle walls 50 in the open position. The opposing walls 50 of the cradle 48 then close about the fitting 12c, placing the adhesive member 24c in contact with the outer surface of the fitting 12c thereby securing the fitting 12c to the retainer 30c.

FIGS. 9–12 illustrate a medical line securement device 8d in accordance with another embodiment of the present invention. The above description with respect to the embodiment of FIGS. 1 and 2 applies equally to the embodiment of FIGS. 9–12, unless otherwise indicated like reference numerals are used to indicate like features among the embodiments, with the letter "d" added to refer to features of the present embodiment.

The retainer 30d comprises a clamping mechanism formed by a pair of opposing latches 62. The latches 62 are spaced apart from each other on the base 34d, and the adhesive member 24d is located between the latches 62. In the illustrated embodiment, the latches 62 and base 34d are integrally formed together in the form of a unitary retainer 30d, such as, for example, but without limitation, by molding, extracting, or thermal forming, and the adhesive member 24 is applied in any of the above-described manners.

Each latch 62 includes a tang 64, which projects toward the other latch 62, and a generally upright support 66, which suspends the tang 64 above the base 34d. An actuator or lug 68 is attached to the support 66 at a point above the base 34d. The actuator 68 desirably includes a roughened upper surface and/or friction ridges in order to enhance frictional contact between the actuator 68 and the user's finger tips. In the illustrated embodiment, each actuator 68 lies to the outer lateral side of the corresponding tang 64 at the top of the upright support 66. In this position, movement of the actuator 68 toward the base 34d causes the support 66 to flex and moves the tang 64 away from the other latch 66, as seen in FIG. 11.

In the illustrated embodiment, the upright supports 66 have elongated shapes and are arranged on the base 34d generally parallel to each other. The supports 66, together with the base 34d, define a generally rectangular channel 70. The opposing tangs 64 of the latches 62 reduce the size of the channel's upper opening. The floor of the channel 70 defines at least a portion of the receiving surface 36d of the retainer 30d.

The channel 70 is sized to receive the catheter fitting wings 18d, and the latches 62 are arranged on the base 34d to snap over the wings 34d to latch the catheter fitting 12d within the channel 70.

In operation, both actuators 68 are depressed by finger pressure, as schematically illustrated in FIG. 11, causing the supports 66 to bend laterally outward. This outward bending of the supports 66 allows lateral wings 18d of the catheter fitting to be placed between the supports 66, thereby bringing a medial surface 22d of the fitting 12d in contact with the adhesive pad 24d. After insertion of the catheter fitting wings 18d into the channel 70, the finger pressure on the actuators 68 can be released, thereby allowing the tangs 64 to partially cover an upper surface of the catheter fitting wings 18. Accordingly, the fitting 12d is secured to the retainer 30d in two ways: first, by the adhesive force of the adhesive member 24d to the medial surface 22d of the fitting 12d; and second, by the placement of tangs 64 over top of the fitting wings 18d.

Figure 13:
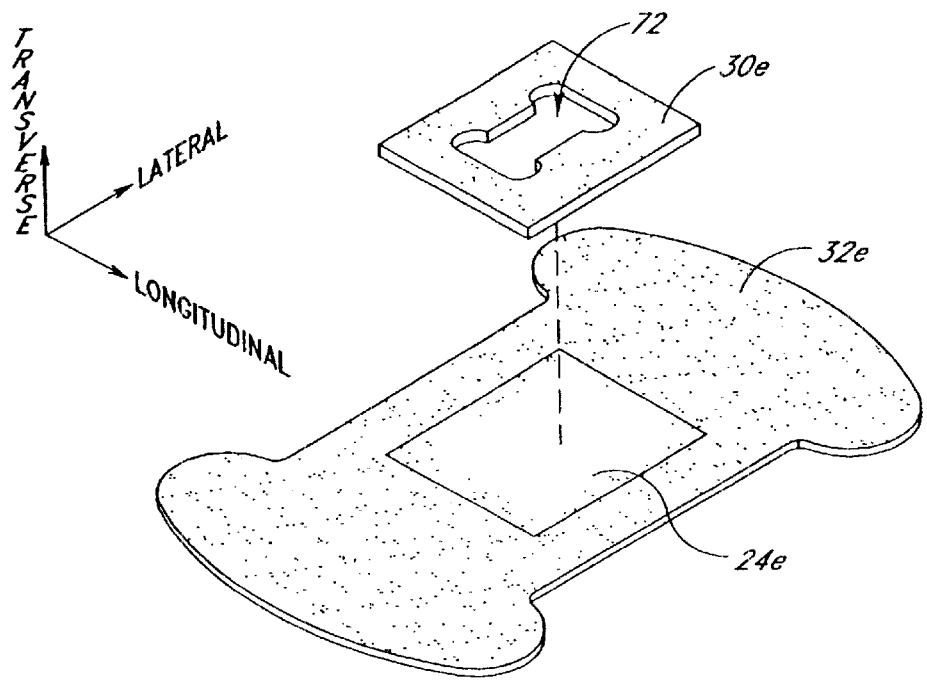
FIG. 13 is a partially exploded perspective view of a securement device configured in accordance with another preferred embodiment of the present invention.
Figure 14:
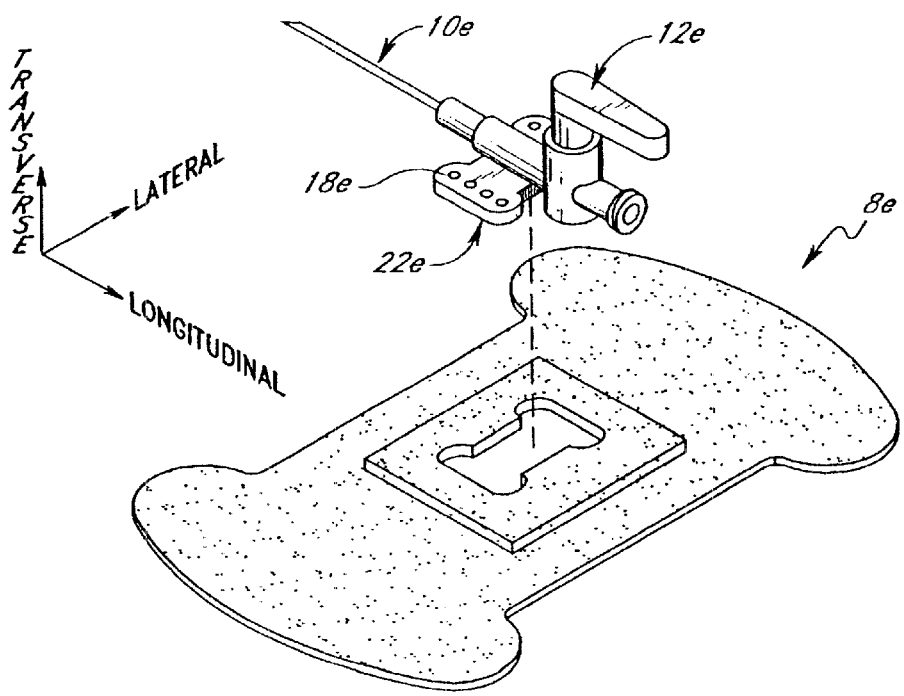
FIG. 14 is a perspective view of the securement device of FIG. 13 in an assembled form and illustrates a catheter fitting positioned above the securement device.

FIGS. 13–14 illustrate a medical line securement device 8e in accordance with another embodiment of the present invention. The above description with respect to the embodiment illustrated in FIGS. 1 and 2 applies equally to the embodiment of FIGS. 13–14, unless otherwise indicated. Like reference numerals are used to indicate like features among the embodiments, with the suffix "e" added to refer to features of the present embodiment.

The retainer 30e comprises plate with a recess or well formed therein. The plate can be formed of any of a wide variety of materials, including a plastic polymer. In the illustrated embodiment, however, the retainer 30e comprises a foam pad defining an aperture 72 therethrough. As shown in FIG. 14, the aperture 72 has a shape corresponding to the shape of a catheter fitting's foot print, and thereby locates the catheter fitting 12e relative to the retainer 30e.

An adhesive member 24e is applied to an anchor pad 32e generally at the center of the pad 32e. The size and shape of the adhesive member 24e desirably matches the size and shape of the foam pad 30e. The adhesive member 24e desirably has a uniform thickness and covers the entire area within its perimeter. As a result, a portion of the adhesive member 24e is exposed through the opening. A release layer (not shown) or the product packaging desirably covers the adhesive ember 24e prior to use, as described above.

The foam pad retainer 30e and its aperture 72 can be formed during a conversion process during a die cut procedure. The application of the adhesive member 24e and the attachment of the foam pad retainer 30e to the adhesive member 24e can also occur as steps during the conversion process.

Although not illustrated, the well or recess need not extend entirely through the foam pad, but rather can take the form of an embossment. In this form, the adhesive member can be applied to the floor of the recess so as to be accessible from a side of the anchor pad opposite of the patient's skin. Again, at least a portion of the recess is configured to correspond to the secured portion of the catheter fitting wings in shape and size.

In operation, the catheter fitting 12e is moved toward and placed into the recess 72 so as to position a medial surface 22e of the fitting 12e relative to the adhesive member 24e. The medial surface 22e is thence pressed into contact with the adhesive member 24e to secure the catheter fitting 12e to the securement device 8e. The anchor pad 32e is secured to the patient's skin in the manner described above.

Figure 15:
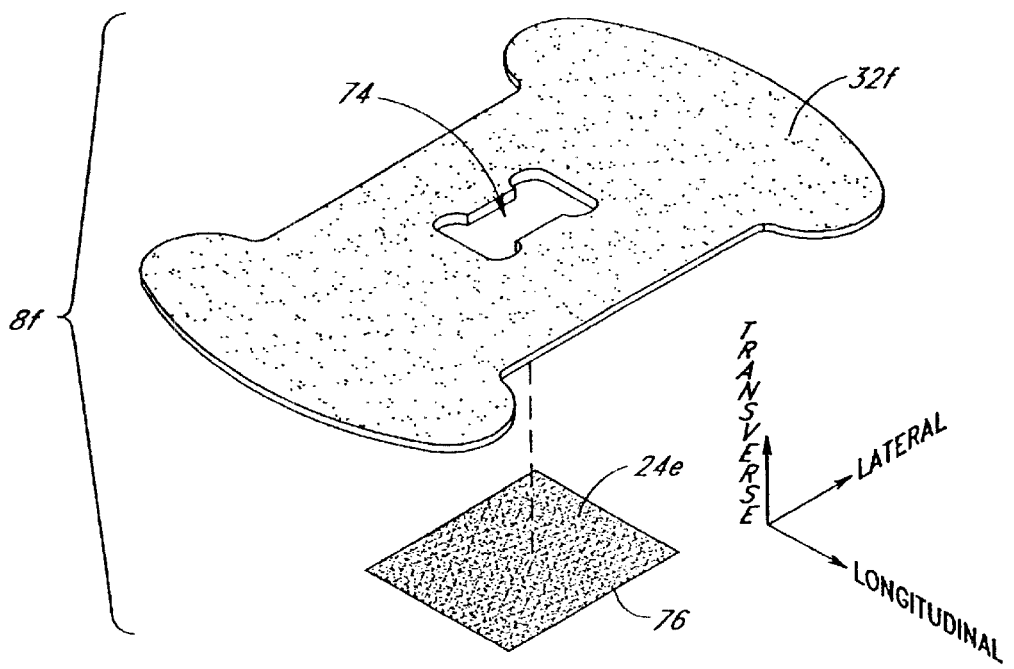
FIG. 15 is a partially exploded perspective view of a securement device configured in accordance with an additional preferred embodiment of the present invention.
Figure 16:
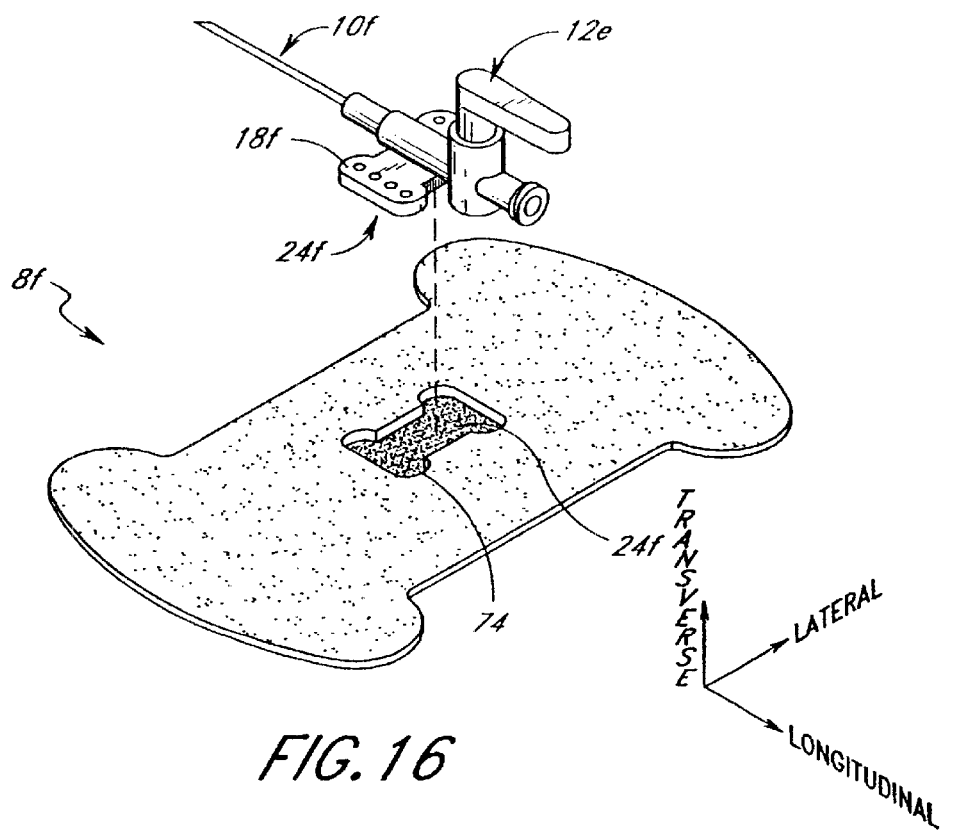
FIG. 16 is a perspective view of the securement device of FIG. 15 in an assembled form and illustrates a catheter fitting positioned above the securement device.

FIGS. 15–16 illustrate a medical line securement device 8f in accordance with another embodiment of the present invention. The description of the embodiment of FIGS. 1 and 2 applies equally to the embodiment of FIGS. 15–16, unless otherwise indicated. Like reference numerals are used to indicate like features among the embodiments, with the suffix "f" added to refer to features of the present embodiment.

This embodiment is also similar to that illustrated in FIGS. 13–14, except that the need for a retainer. The retainer illustrated in FIG. 13 is eliminated in the present embodiment, and a recess or well 74 is defined in the anchor pad 32f itself. In the illustrated embodiment, the recess 74 extends entirely through the anchor pad 32f, however, the recess can take the form of an indentation in the pad 32f. In either case, the recess 74 desirably has a similar shape and size to at least a portion of the catheter fitting 12f. And preferably, the recess 74 generally matches the foot print of the catheter fitting 12f in shape and size.

The adhesive member 24f is located on the bottom of the recess. In the illustrated embodiment, though, where the recess extends through the pad 32f, a substrate 76 supports the adhesive member 24f at this location. The adhesive member 76 desirably covers the entire substrate 76 and secures it to a side of the anchor pad on which the adhesive layer is formed. Thus, the substrate can include adhesive layers on both of its sides.

The use of the present securement device 8f is similar to that associated with the securement device illustrated in FIGS. 13 and 14. The catheter fitting 12f is moved toward and placed into the recess 74 so as to position a medial surface 22f of the fitting 12f relative to the adhesive member 24f. The medial surface 22f is thence pressed into contact with the adhesive member 24f to secure the catheter fitting 12f to the securement device 8f. The anchor pad 32f is secured to the patient's skin in the manner described above.

As common to all of the embodiments described above, the securement device includes adhesive layers on two sides. One side adheres to the patient, while the other side adheres to the medical line or article. In order to properly position the medical line on the securement device and to enhance the speed and ease of applying the securement device, each of the above-described securement devices also include a locator mechanism. Proper positioning promotes good contact between the adhesive member and the medical line or article to enhance securement, as well as ensures that the medical line or article completely covers the adhesive member. As a result, the adhesive tends not to become a sites for bacterial growth. The locator mechanism also allows the health care provider to properly position the medical line or article on the securement device with minimum time and effort.

For use with catheter type devices, each of the securement devices described above secures the catheter fitting to the patient, rather than secures the connector on the tubing to the patient as done by prior devices. The catheter thus does not move with movement of an anatomic joint when an interconnection between the catheter and the tubing spans across the joint.

Also as common to each of the above-described embodiments, the securement device provides a sterile, stable, efficient way to anchor a medical line or article to a patient. The securement device is quickly and easily applied to the medical line or article by using the locator mechanism, and is equally quickly and easily applied to the patient's skin. During the application process, the health care provider need not contact the adhesive layers with his or her gloves. Use of the securement device thus does not degrade glove protective. Once secured, the securement device stabilizes the catheter and substantially prevents catheter movement and migration.

Although not illustrated, each of the above-described securement devices can include one or more tube clips, especially for use with intravenous catheters. An exemplary tube clip is described and illustrated in U.S. Pat. No. 5,578,013, issued in the name of Steven F. Bierman, on Nov. 26, 1996, and to the assignee hereof, which is hereby incorporated by reference. The tube clip can have a plate-like base adhered to the anchor pad and be located on either side of the retainer to accommodate left or right hand mounting.

The tube clip desirably defines a channel having a generally circular cross-sectional configuration truncated to form an upper orifice. The diameter of the channel is desirably slightly less than that of the fluid supply tube so as to ensure a secure interconnection. The channel receives a portion of the fluid supply tube through the orifice upon application of gentle pressure or by pulling the tubing across and through the orifice of the tube clip. The clip surrounds a substantial portion of the tubing with the tubing positioned within the channel.

In use, a health care provider loops the IV supply tubing around from the insertion site and insert a portion of the tubing into the tube clip. The looped section has sufficient slack to form a conventional safety loop. The safety loop absorbs any tension applied to the fluid supply tube to inhibit pulling of the catheter.

The skilled artisan will also recognize the interchangeability of various features from different embodiments. For instance, the angular orientation of the receiving surface illustrated in FIG. 3 can be employed with the cradles illustrated in FIGS. 4 and 5. Thus, various features of the embodiments can be combined in order to adapt the securement device to a particular application.

Although this invention has been described in terms of certain preferred embodiments, other embodiments apparent to those of ordinary skill in the art are also within the scope of this invention. Accordingly, the scope of the invention is intended to be defined only by the claims that follow.

What is claimed is:

1. A method of manufacturing a securement device for retaining a medical line to the body of a patient comprising:
   affixing a sheet of a backing material to a sheet of adhesive-backed foam material;
   creating a recess in the foam material on the side opposite the side to which the sheet of backing material is affixed, the recess defining at least two surfaces that extend generally normal to the surface of the foam material, the two surfaces spaced apart by a distance at least as great as a lateral dimension of the portion of the medial line retained by the securement device so as to form
   a locator mechanism adapted to interact with a the portion of the medical line and thereby guide the medical line into a position relative to the recess; and
   applying a patch of an adhesive material to the foam material on the side opposite the side to which the sheet of backing material is affixed, the patch of adhesive being located so as to lie at least partially between the two surfaces once the securement device is formed.

2. A method of manufacturing a securement device as in claim 1, wherein the adhesive patch is applied by spray-sputtering an adhesive onto the upper surface of the retainer.

3. A method of manufacturing a securement device as in claim 1, wherein the adhesive patch is applied by transferring the adhesive patch to the retainer using transfer tape.

4. A method as in claim 1, wherein one of the at least two surfaces is aligned substantially parallel to the axis of the medical line when the medical line is retained.

5. A method as in claim 1, wherein one of the at least two surfaces is aligned substantially normal to the axis of the medical line when the medical line is retained.

6. A method of manufacturing a securement device for retaining a medical line to the body of a patient comprising:
   cutting a foam sheet into an anchor pad;
   cutting through the foam sheet so as to form an, aperture being positioned on the anchor pad and having at least two surfaces extending normal to the surface of the anchor pad;

attaching a substrate to the foam pad; and applying a layer of adhesive so as place the adhesive layer such that, once the securement device is formed, at least a portion of the adhesive layer is accessible through the aperture.

7. A method of manufacturing a securement device as in claim 6, wherein the layer of adhesive is applied by spray-sputtering an adhesive onto the substrate.

8. A method of manufacturing a securement device as in claim 6, wherein the layer of adhesive is applied by transferring the adhesive to the substrate using transfer tape.

9. A method of manufacturing a securement device as in claim 6 additionally comprising corona-treating the upper surface of the foam pad with a low electric charge.

10. A method of manufacturing a securement device as in claim 6, wherein the substrate is attached to the foam pad using a solvent bond adhesive.

11. A method of manufacturing a securement device as in claim 6, wherein the substrate comprises a double sided adhesive tape.

12. A method as in claim 6, wherein one of the at least two surfaces is aligned substantially parallel to the axis of the medical line when the medical line is retained.

13. A method as in claim 6, wherein one of the at least two surfaces is aligned substantially normal to the axis of the medical line when the medical line is retained.

14. A method of manufacturing a securement device for retaining a medical line to the body of a patient, the medical line having an elongated body and a fitting including at least one laterally extending surface that projects beyond the elongated body of the medical line to at least one side of the medical line, comprising:

providing an anchor pad having an upper and a lower surface;

attaching a substrate to the lower surface of the anchor pad;

creating a recess in the upper surface of the anchor pad so as to form at least two surfaces oriented generally normal to the upper surface of the anchor pad and being spaced apart by a distance at least as great as a dimension of the laterally extending surface of the fitting, and also so as to form a mounting surface which is accessible from an upper side of the anchor pad, the mounting surface having an adhesive member extending at least partially between the at least two surfaces and disposed so as to be accessible from the upper side of the anchor pad.

15. A method as in claim 14, herein one of the at least two surfaces is aligned substantially parallel to the axis of the elongated body of the medical article when the medical article is retained.

16. A method as in claim 14, wherein one of the at least two surfaces is aligned substantially normal to the axis of the elongated body of the medical article when the medical article is retained.

17. A method as in claim 14 wherein the at least two surfaces are disposed so as to generally match the size and shape of the laterally extending surface of the fitting.

18. A method as in claim 14 wherein the adhesive member is sized so as to be completely covered by the fitting of the medical line when the medical article is retained.

* * * * *